United States Patent [19]

Samain et al.

[11] 4,189,614
[45] Feb. 19, 1980

[54] PROCESS FOR THE STEREO SPECIFIC PREPARATION OF SEXUAL PHEROMONES

[75] Inventors: Daniel Samain, Compiegne; Charles Descoins, Bailly; Gerhard Kunesch, Orsay, all of France

[73] Assignee: Institut National de la Recherche Agronomique, Paris, France

[21] Appl. No.: 12,132

[22] Filed: Feb. 14, 1979

[30] Foreign Application Priority Data

Feb. 15, 1978 [FR] France ................. 78 04257

[51] Int. Cl.² .............................................. C07C 33/02
[52] U.S. Cl. ........................... 568/908; 260/345.9 R; 260/347.8; 260/448.2 B; 568/628; 568/687; 568/840
[58] Field of Search .................... 568/876, 840, 908

[56] References Cited

U.S. PATENT DOCUMENTS

| | | | |
|---|---|---|---|
| 3,783,135 | 1/1974 | Henrick et al. | 568/908 |
| 3,818,049 | 6/1974 | Henrick et al. | 568/908 |
| 3,825,607 | 7/1974 | Descoins et al. | 568/841 |
| 3,856,866 | 12/1974 | Henrick et al. | 568/841 |
| 3,910,897 | 10/1975 | Chodnekar et al. | 568/876 |
| 3,919,329 | 11/1975 | Anderson et al. | 568/908 |
| 3,943,157 | 3/1976 | Henrick et al. | 568/908 |
| 3,953,532 | 4/1976 | Anderson et al. | 568/908 |
| 4,002,684 | 1/1977 | Fraunberg | 568/876 |
| 4,061,667 | 12/1977 | Schleppnik | 568/876 |

FOREIGN PATENT DOCUMENTS

| | | | |
|---|---|---|---|
| 961862 | 1/1975 | Canada | 568/840 |
| 456516 | 2/1977 | U.S.S.R. | 568/876 |

*Primary Examiner*—Joseph E. Evans
*Attorney, Agent, or Firm*—Cushman, Darby & Cushman

[57] ABSTRACT

A process for the stereoselective preparation of sexual pheromones is disclosed. The process involves reacting a compound of the formula

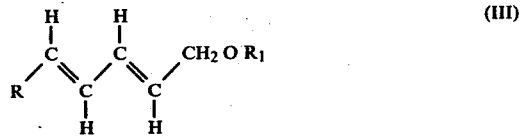

(III)

in which the conjugated diene is of the trans-trans (E—E) stereochemical configuration with a compound of the formula

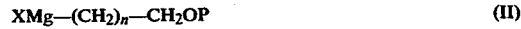

(II)

11 Claims, No Drawings

PROCESS FOR THE STEREO SPECIFIC PREPARATION OF SEXUAL PHEROMONES

The present invention has for an object a process for the stereoselective preparation of sexual pheromones, and in particular, of pheromones which are alcohols and have a conjugated diene moiety, the stereochemical configuration of which is trans-trans (E—E).

Synthetic sexual pheromones have been the object of research because of the great interest of these substances for use in the struggle and control of principle lepidoptera predators of fruit orchards.

In this regard, the work of H. Audemard and coll. is noted in the Review of Agricultural Zoology and of Vegetable Pathology (Revue de Zoologie Agricole et de Pathologie Vegetale) 76, 15–24, 1977, which reports the struggle against the Carpocapse (Laspeyresia Pomonella L.) by using a sexual pheromone of known synthesis, commercially known as Codlemone (or dodecadiene-8E, 10E ol-1), in apple orchards in a method referred to as "confusion of males".

The principle of this method resides in diffusing a quantity of pheromones into a section of the orchard to permeate the atmosphere uniformly with vapors of the pheromone substance. Male insects fly to such an environment and are incapable of localizing the female of the attract scent (of the pheromone). The female population available for fertilization is reduced in concentration at least proportionately to the increase in the male population in the treated section of the orchard. Ultimately, this process results in diminution of the insect population, from generation to generation, and eventual total elimination thereof.

This method of controlling the predators of the fruit orchards represents the interest that the pheromones present as sexual attractants, since in the case of the Carpocapse, it has been established that the Carpocapse attacks affect at least 0.5% of the fruits.

This method is not yet a generally established method of control because the methods for synthesizing sexual pheromones of principle predators are lengthy, that is to say, comprehend numerous steps, and, moreover, the products obtained are not always of the desired stereochemical purity.

It follows that numerous purifications are then necessary which inevitably lead to a high price for this type of compounds.

Thus, the sexual pheromones are not yet an arsenal or means of combat and control for arboriculturists.

The different sexual pheromones isolated, identified and synthesized to date, reflect that they are molecules of low molecular weight with linear unsaturated hydrocarbon chains, generally mono- or bi-unsaturated, which also contain an alcohol function, an acetate or an aldehyde group.

The research which has been undertaken does demonstrate the capital importance of the cis or trans (Z or E) configuration of the unsaturated moieties of the pheromones in the action of "confusion" by the sexual pheromones so far synthesized.

Indeed, it has been established that the stereochemical factor can, itself alone, assure the specificity of the signal with respect to the males.

Moreover, it has been noted that use of sexual pheromones contaminated by synthesis by one or more other isomers even in relatively small quantity, reduces the action of the active isomer considerably, sometime to the point of being totally inhibited.

Thus, it is important that the methods of synthesizing the sexual pheromones are totally stereoselective, that is to say, do not lead to secondary reactions of isomerization which produce mixtures of isomers.

Moreover, this type of synthesis ought to include only a few steps which are characterized by good yields, to produce intermediate products easily and, in particular, to produce products of commerce.

The present invention is directed to a new process of stereoselectively preparing sexual pheromones of great stereochemical purity and, in particular, to pheromones having an alcohol group and a conjugated diene group of the trans-trans (E—E) stereochemical configuration corresponding to the following general formula:

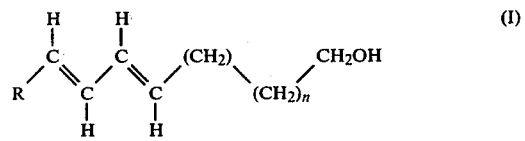

in which:
R represents a saturated linear alkyl radical having from 1 to 4 carbon atoms and n is a number from 1 to 5.

Various syntheses of the compounds of this type and notably of Codlemone, R=CH$_3$ and n=5 (dodecadiene-8E, 10E ol-1) have already been proposed in the literature.

In particular, reference is made to the syntheses of Codlemone by Zoecon Corporation which is described in U.S. Pat. No. 3,825,607, and that of K. Mori described in *Tetrahedron*, Vol. 30, p. 1807–1810 (1974).

In these syntheses, the principle step consists of either coupling a C$_7$ moiety (bromo-1 heptadiene-3E,5E) and a C$_5$ moiety (magnesium compound of [chloro-5' pentyloxy]-2 tetrahydropyranne) or coupling a C$_6$ moiety (bromo-1 hexadiene-2E, 4E) and another C$_6$ moiety (a magnesium compound of [chloro-6' hexyloxy]-2 tetrahydropyranne).

In the course of the coupling reaction between the C$_7$ moiety and the C$_5$ moiety, there is produced a partial isomerization product leading to an isomeric mixture in which the trans-trans is, however, preponderant.

Likewise, in coupling between the C$_6$ moiety and the other C$_6$ moiety, referred to above, isomerization also occurs accompanied by a transposition of the allylic moiety.

Thus, in the two foregoing syntheses, the production of the trans-trans isomer in the pure stereochemical state necessitates purification and, in effect, these syntheses produce Codlemone in relatively small yields.

Moreover, the methods of purification which are easily realized on a laboratory scale are difficult when transposed to industrial scale.

After lengthy research, it has been surprisingly and unexpectedly established that the sexual pheromones of formula I above can be obtained in a simple fast manner in excellent yields and in a state of great stereochemical purity by coupling a magnesium derivative and an acetate, tosylate, or mesylate of an alcohol containing a conjugated diene of the trans-trans stereochemical configuration under particular conditions of reaction, including, notably, the temperature of coupling and the proportions of the reactants used.

The subject research has, in effect, proved that excellent yields and the retention of stereochemical configuration are only possible in the coupling reaction, when the precursor diene is uniquely of the trans-trans configuration.

Indeed, it has been established that, if the precursor diene is cis-trans (Z, E), cis-cis (Z, Z) or trans-cis (E, Z), there is no retention of stereochemistry, and the course of the reaction leads to the production of a mixture of isomers.

The present invention has for an object a new process of stereoselective preparation of sexual pheromones having an alcohol group and a conjugated diene of the trans-trans (E—E) stereochemical configuration corresponding to the following general formula:

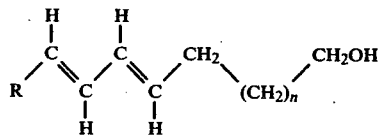

in which:

R represents a saturated linear alkyl radical having 1 to 4 carbon atoms and n is a number from 1 to 5, wherein in a first stage, there is prepared in a tetrahydrofuran medium, a magnesium derivative corresponding to the following formula:

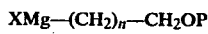

$$XMg-(CH_2)_n-CH_2OP$$

in which:

X represents a halogen, preferably Br or Cl, and P is a protective group, and wherein, in the second stage, at a temperature of from 0° to −20° C., the said magnesium derivative is added in excess to a tetrahydrofuran solution containing a catalyst of copper and a trans-trans diene compound corresponding to the following formula:

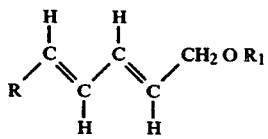

in which:

R has the same meaning as above and $R_1$ represents a $-COCH_3$, $-SO_2CH_3$ or $-SO_2C_6H_4CH_3$ group and wherein the product of reaction is subjected to a hydrolysis reaction to liberate the protective group.

This process of preparation permits, in particular, the synthesis of compounds of formula (I) in which:

(1) $R=CH_3$ and $n=5$, dodecadiene 8E, 10E, ol-1 (Codlemone),
(2) $R=C_2H_5$ and $n=4$, dodecadiene −7E, 9E ol-1,
(3) $R=C_3H_7$ and $n=3$, dodecadiene −6E, 8E ol-1, and
(4) $R=C_4H_9$ and $n=4$, tetradecadiene −7E, 9E ol-1, These compounds are obtained by the process according to the invention in a yield of 60% or more and with a stereo chemical purity equal to or greater than 98% in the trans-trans isomer.

The magnesium derivatives of formula (II) are easily obtained from the corresponding halogenalkanols w—w' in which the OH function has been protected by the aid of a protecting or blocking group.

Those halogenalkanols w—w' which can be used are those which are available commercially and include chloro- or bromo-3 propanol-1, chloro- or bromo-4 butanol-1, chloro- or bromo-5 pentanol-1, chloro- or bromo-6 hexanol-1 and the chloro- or bromo-7 heptanol-1.

The protective group for the OH function of the halogenalkanols can be groups which form bonds of the acetal type, such as tetrahydropyrannyl and tetrahydrofurannyl groups, as well as certain silyl groups, such as trimethylsilyl and triethylsilyl.

Other protective groups can also be utilized such as triphenylmethyl, diphenylmethyl, benzyl or t-butyl.

According to one particular embodiment of realizing these products, a protective group such as the tetrahydrofurannyl or tetrahydropyrannyl is preferably employed.

The compounds of formula (II) have been easily obtained by reacting the corresponding halogenoalkanols w—w' with dihydrofuran or dihydropyran in the presence of acid catalyst, and, in particular, in the presence of a strong acid such as hydrochloric acid, or p-toluene sulfonic acid, sulfuric acid or methanesulfonic acid.

The compounds of formula (III) are equally easily obtained from the corresponding dienic-2E, 4E alcohols from the classical reactions for forming acetoxy, mesyl and tosyl derivatives.

According to a preferred embodiment of the invention, the acetoxy derivatives are obtained by acetylation of dienic-2E, 4E alcohols with acetic anhydride in pyridine.

The dienic-2E, 4E alcohols which can be used to make compounds of formula (III) include hexadiene-2E, 4E ol-1, heptadiene-2E, 4E ol-1, octadiene-2E, 4E ol-1 and nonadiene-2E, 4E ol-1.

The dienic alcohols are for the most part available commercially and are sold notably by the Société Oril.

According to the invention, the copper catalyst can be copper iodine, copper chloride, or copper bromide or dilithium tetrachlorocuprate ($Li_2Cu Cl_4$).

According to a preferred embodiment of the invention, the process employs the latter catalyst which is obtained by reacting lithium chloride and copper chloride together in a molar ratio of 2:1 according to method described by Tamura et coll. in *Synthesis*, July 1971, page 303.

In general, according to the invention, a catalystically effective amount of catalyst is employed, which can range from 0.01 to 0.06 mole, and preferably about 0.04 mole, per mole of compound of formula (III).

As indicated above, the temperature of the addition of the magnesium is significant and ought to be in a range of from 0° to −20° C., and preferably about −10° C.

After the addition of magnesium to the tetrahydrofuran solution of the compound of formula (III), the final concentration of the reactants in tetrahydrofuran ought to be from about 0.1 N and 0.8 N, and preferably at about 0.5 N. Then, the reaction of coupling is allowed to occur at ambient temperature for a period of from 1 to 5 hours, and preferably for a period of about three hours.

As indicated above, in order to obtain excellent yields, it is important to use the magnesium compound of formula (II) in excess with respect to the molar ratio of the compound of formula (III), this excess being at least 0.2 mole of magnesium per mole of the compound of the formula (III), and preferably from 0.25 to 0.6 mole.

After the end of the coupling reaction, the reaction mixture is hydrolyzed at a temperature from 0° to −20° C., and preferably at about −10° C., with a stoichiometric quantity of a saturated solution of ammonium chloride.

The intermediate compound formed has the formula:

(IV)

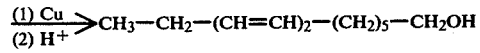

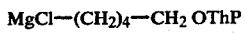

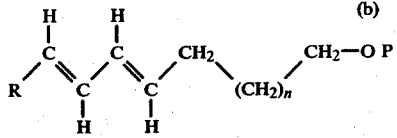

in which:

R, n and P have the definitions set forth above; after evaporation of the reaction solvents and extraction, said compound is subjected to a hydrolysis to liberate the protective group and to produce the compound of formula (I).

The nature of the hydrolyzing agent and the conditions of hydrolysis depend on the nature of the protective group.

When the protective group is a tetrahydropyrannyl or tetrahydrofurannyl group, preferably p-toluene sulfonic acid in an alcohol (methanol) medium is employed in the hydrolysis which is conducted at a temperature that is generally from 20° to 60° C.

When the protective group is a silyl group, it can be eliminated by the technique described in J. Am. Chem. Soc., 74.3024 (1952).

After the hydrolysis step, the residue, remaining after the evaporation of solvents used in the extraction, is submitted to a distillation under reduced pressure to obtain the compound of formula (I) in the purified form.

Certain alcohols of the formula (I) obtained by the process according to the invention can be the crystalline form; and it is thus possible to obtain them in purified form by crystallization in an appropriate solvent, for example, in a hydrocarbon, such as pentane or hexane.

The conjugated dienic alcohols of formula (I) obtained by the process according to the invention can, if necessary, be subjected to other transformations and notably can be transformed into acetates, propionates, butyrates and isobutyrates according to conventional methods and even into corresponding aldehydes by an oxidation reaction with the aid of pyridinium perchlorate.

The derivatives are in effect sexual attractants for a number of lepidoptera.

With the object of showing that the excellent stereoselectivity of the process of the invention is possible only when the compounds of formula (IV) is of trans-trans (E—E) stereochemistry, they have realized in the same operative conditions the following coupling reactions:

from the isomers 2E 4-E, 2-E 4-Z, 2-Z 4-Z and 2-Z 4-E from acetoxy-1 heptadiene-2,4 (a).

After hydrolysis and distillation under reduced pressure, gas-liquid chromatography (GLC) of four preparations gives the following results:

| Stereochemistry of acetoxy-1 heptadiene-2,4 of a purity which is greater than 98% | Temperature of magnesium addition | Excess of magnesium (mole) | Dodecadiene-7, 9 ol-1 obtained (%) | | | |
|---|---|---|---|---|---|---|
| | | | Iso. 7Z,9E | Iso. 7E,9Z | Iso. 7Z,9Z | Iso. 7E,9E |
| 2E,4E | −10° C. | 0.5 | 0 | 0 | 0 | 100 |
| 2E,4Z | " | " | 0 | 75 | 0 | 25 |
| 2Z,4Z | " | " | 3 | 27 | 60 | 10 |
| 2Z,4E | " | " | 61 | 2 | 1 | 36 |

Thus, it is established that only the coupling realized between the reactant acetoxy-1 heptadiene-2E, 4-E leads to retention of stereochemistry in the resulting Dodecadiene-7,9 ol-1.

Now the invention is illustrated, without limiting the nature thereof, by various examples of preparing sexual pheromones of formula (I) by the process according to the invention.

EXAMPLES

EXAMPLE 1

Preparation of Acetoxy-1 hexadiene-2E, 4E: $C_8H_{12}O_2=140$ (formula III, $R=CH_3$ $R_1=-COCH_3$)

1 kilogram of hexadiene -2E,4E ol-1 (having a stereochemical E,E purity of 98%) is dissolved in 2.8 liters of pyridine (distilled over potassium). The solution is cooled to about 10°; and then add over a period of two hours, 2.8 liters of acetic anhydride, is added. At the end of the addition, the temperature is allowed to increase to +20° for a period of three hours. The reaction mixture is then poured onto 10 kg of crushed ice and then it is extracted two times with two liters of technical grade pentane. The organic phase is successively washed with water (500 cm³), with 2 N sulfuric acid (500 cm³), a saturated solution of sodium bicarbonate (500 cm³), again with water, and finally with a saturated solution of sodium chloride (500 cm³). After drying over magnesium sulfate and evaporating the pentane, the distillation of the residue yields 1.633 kg of acetate (81%) bp=78° C. at 20 mm of Hg pressure.

According to the same mode of operation, acetoxy-1, heptadiene -2E,4E is prepared, starting from heptadiene-2E,4E ol-1 with a yield of 80%, bp=85° C./20 mm.

EXAMPLE 2

Preparation of (6'-chloro hexyloxy)-2 tetrahydropyranne: $C_{11}H_{21}O_2Cl=220.5$ 3 kg of chloro-6 hexanol-1, of commercial grade, are passed into a 10 liter reaction vessel and 7.5 cm$^3$ of concentrated hydrochloric acid is added. The reaction mixture is cooled to about +10° by a brine (crushed ice and methanol); and over a period of three hours, in portions of 100 cm$^3$, 2 kg 125 of freshly distilled dihydropyran. After the end of the addition, the reaction mixture is left for three hours at ambient temperature, it is diluted with 2 liters of ether and the reaction mixture is washed successively with 500 ml of 2 N sodium hydroxide, 2 liters of water, and 2 liters of a saturated solution of sodium chloride.

It is dried over magnesium sulfate, the ether is evaporated, and the residue is distilled under reduced pressure.

They obtain: an intermediary fraction of 400 g bp=40°–106° C. at 0.1 mm of Hg pressure and a principle fraction corresponding to the product of 4 kg 311 (Yield 91%); bp=106°–110° C. at 0.1 mm of Hg pressure.

The product is characterized by the I.R. spectrum:
IR (film); bands: 2930, 2860, 1460, 1450, 1440, 1350, 1200, 1130, 1120, 1075, 1030, 900, 865, 810 cm$^{-1}$.

EXAMPLE 3

Preparation of the tetrahydropyrannyl ether of dodecadiene-8E, 10E ol-1 (formula IV, R=CH$_3$, n=5 and P=tetrahydropyrannyl)

The reactions (a) and (b) below were conducted in Argon.

(a) Preparation of magnesium (chloro-6' hexyloxy)-2 tetrahydropyran.

In a reaction vessel of about 4 liters equipped with an agitation means, an addition funnel and a cooled reflux condenser, 60 g of magnesium shavings that are recovered from 100 ml of tetrahydrofuran (THF) are introduced in one addition, 10 g of (chloro-6' hexyloxy)-2 tetrahydropyranne obtained according to Example 2 is added; and the reaction mixture is brought to reflux. Ebullition begins; 5 cm$^3$ of dibromoethane is added; a very violent reaction results with attack of the magnesium and blackening of the reaction mixture. Agitation is then begun; and while maintaining the reflux, a solution of 425 g of (chloro-6' hexyloxy)-2 tetrahydropyran in 1.6 liters of tetrahydrofuran is introduced over a two-hour period, dropwise.

At the end of the addition, the reaction mixture is allowed to reflux yet another three hours and is left overnight at ambient temperatures.

(b) The coupling reaction between acetoxy-1 hexadiene-2E, 4E prepared according to Example 1 and the preceding magnesium preparation:

Into a reaction vessel of approximately 6 liters capacity equipped with a stirring means and a thermometer, a solution of 180 g acetoxy-1 hexadiene-2E,4E in 1.5 liters of tetrahydrofuran is siphoned.

The reaction mixture is cooled to −10°; a solution of 4.3 g of lithium chloride (anhydrous) and of 6.8 g of copper chloride (anhydrous) in 90 cm$^3$ of tetrahydrofuran is added by siphoning. The reaction mixture is red orange in color.

Then, over a period of one and one half hours, the preceding magnesium solution is added, while insuring that the temperature does not exceed −10° C. At the end of the addition, the reaction mixture is a clear green color, then it becomes almost clear and, finally, turns a black violet.

At the end of the addition, it is left for three hours at 0° C., cooled again to −10° C., and then hydrolyzed with a saturated solution of ammonium chloride with violent agitation, until the solution becomes clear when an abundant black viscous precipitate is found at the bottom of the reaction flask. The supernatatant is decanted and the residue is triturated with 3 volumes of 200 cm$^3$ of ether. The organic phases are admixed, washed successively with saturated ammonium chloride (500 cm$^3$: 2 times) and then with the saturated solution of sodium chloride (500 cm$^3$: 2 times).

The organic phases are then transferred directly into an evaporator.

After evaporation of the solvent under partially reduced pressure (50 mm), they obtain 470 g of residue, constituted essentially of the tetrahydropyrannyl ether of dodecadiene-8E, 10E, ol-1.

EXAMPLE 4

Preparation of dodecadiene-8E,10E ol-1: (formula I, R=CH$_3$ and n=5)

The residue obtained in Example 3 is dissolved in 2.5 liters of methanol and 250 cm$^3$ of water and then 42 g of p-toluene sulfonic acid is added. It is heated to 60° for a period of three hours and left overnight at ambient temperature. A great part of the methanol is evaporated under reduced pressure, leaving a residue which is admixed two times its volume of ether and it is washed successively with water (300 cm$^3$), with a saturated solution of sodium bicarbonate (300 cm$^3$), again with water, and lastly, with a saturated solution of sodium chloride.

It is dried over magnesium sulfate.

After evaporation of the solvent, distillation of the residue (270 g) results in:

59 g of product (b.p=40°–98°/0,1 mm Hg); 140 g of dodecadiene-8E, 10E ol-1 (b.p=98°–100°/0,1 mm) which recrystallizes in the course of distillation and 71 g of residue constituted essentially of dodecanediol.

The yield in dodecadiene-8E,10E, ol-1 (distilled and crystallized) is 62.5% calculated on the basis of the acetoxy-1 hexadiene 2E,4E reactant.

The stereochemical purity of this product is 99.5% determined by gas-liquid chromatography (GLC):

Column 5 m inox $\frac{1}{8}''$ 3% F.F.A.P./chrom G.H.P. 80/100°–190° C.: it is characterized:

(i) By its I.R. spectrum (cm$^{-1}$): with bands at 3370 (OH associated); 1615 (—C=C); 1055 (primary OH); 980 (—CH=CH—, E, conjugated). The absence of a band at 950 cm$^{-1}$ denotes the absence of the isomer 8Z, 10E.

(ii) By its N.M.R. spectrum (δ, ppm, 250 Mhz, CDCl$_3$):1.3, S. large 8H, 4CH$_2$; 1, 54, quint, 2H, —CH$_2$ in C$_1$; 7, d, 3H, —C$\underline{H}_3$; 2, 04, q, 2H,= —C$\underline{H}_2$; 3, 6, t, 2H, —C$\underline{H}_2$ OH; 5, 54, m, 2H; H$_{11}$ and H$_8$; 5.96, 2H, H$_9$ and H$_{10}$.

(iii) By its mass spectrum: M+ = 182; fragments at 164 (M+ −H₂O); 135 (M+ =(H₂O+C₂H₅)), 121, 107, 81, 79, 68, 67, 55, 42, 32.

and (iv) By its melting point: m.p.=29°-30°.

According to a variant of the preceding process, it is possible to effectuate the distillation under reduced pressure by isolating the dodecanediol crude product of hydrolysis by taking it up in three times its volume of pentane and leaving it at ambient temperature for three hours. Indeed, under these conditions, the dodecanediol precipitates and is eliminated by drying under reduced pressure.

EXAMPLE 5

Preparation of dodecadiene-8E,10E ol-1 (formula I, R=CH₃ n=5).

According to the same operating conditions as those used in Examples 3 and 4 above, the synthesis of 1,100 kg of dodecadiene-8E,10E ol-1 is undertaken by using the following quantities of solvents and reactants:
3,360 kg of (chloro-6' hexyloxy)-2 tetrahydropyran
480 g of magnesium
1,440 kg of acetoxy-1 hexadiene-2E, 4E
35 g of anhydrous lithium chloride
55 g of anhydrous copper chloride
29 liters of T.H.F., 15 liters of methanol
300 g of p-toluene sulfonic acid In this preparation, the recovery of distilled and crystallized dodecadiene-8E,10E ol-1 was 60%.

The dodecadiene-8E,10E ol-1 can be obtained, if desired, in analytically pure form by following the following procedure:

140 g of dodecadiene 8E,10E ol-1 resulting from the preceding reaction are dissolved in 280 cm³ of pentane (quality nanograde Byke-Mallincrodt). The solution is slowly cooled to −10° C., during which time the dodecadiene-8E, 10E ol-1 crystallizes into white needles.

They are dried at −10° C. and 133 g of dodecadiene-8E,10E ol-1 is obtained rigorously pure according to G.L.C. (same analytical conditions as in Ex4).

Melting point=32° C.

This high purity is not necessary for use in the method of "confusing males" in orchards.

EXAMPLE 6

Preparation of acetoxy-1 octadiene-2E, 4E (formula III, R=C₃H₇ and R₁=—COCH₃)

Octadiene-2E, 4E ol-1 commercial is first recrystalized in cold pentane.

10 g (0.08 mole) of recrystallized alcohol is then acetylated by 16.3 g (0.16 mole) of acetic anhydride in 20 ml of pyridine. After three hours at ambient temperature and hydrolysis by conventional technique, they obtain: 12 g (90%) of the corresponding acetate. b.p.=50°/0,1 mm Hg, GLC: one product only on the column 5% E.C.N.S.S.M. on Gas Chrom Q 100:120 mesh, 3 m inox ⅛, 130°. I.R. (cm⁻¹, film) 1740 (C=O ester), —C=C— 1660, —CH=CH— E conjugated 990(s) and 945(w).

EXAMPLE 7

Preparation of dodecadiene-6E, 8E ol-1 (formula I, R=C₃H₇ and n=3) and its acetylated derivative To the acetate obtained in Example 6 (4 g, 0.023 mole), admixed with 8 ml of a solution of dilithium tetrachlorocuprate prepared as above, is added at −10° an excess of magnesium of (chloro-4' butyloxy)-2 tetrahydropyran (35 cm³ of a N solution in T.H.F.) under the same reaction conditions as those described in Example 3b) above.

After hydrolysis and evaporation of solvent, the residue is treated with p-toluene sulfonic acid in methanol according to the same conditions in Example 4 which produce the dodecadiene-6E,8E ol-1.

This latter substance without being purified is treated with acetic anhydride (3.36 g, 0.033 mole) in the conventional manner and produces 3.3 g (64%) of acetoxy-1 dodecadiene-6E, 8E, b.p.=88°/0,1 mm Hg GLC: one product only on 3% F.F.A.P., Gas Chrom G, 5 m inox ⅛, 190°.

I.R. (cm⁻¹ film) 1740 (C=O ester), 985 (s) and 955 (w) —CH=CH— E conjugated.

EXAMPLE 8

Preparation of acetoxy-1 nonadiene-2E, 4E (formula III, R=C₄H₉ and R₁=COCH₃)

Commercial nonadiene-2E, 4E ol-1 is first recrystallized in pentane.

10 g (0.071 mole) of alcohol is then acetylated by 14.4 g (0.142 mole) of acetic anhydride in solution in 20 ml of pyridine. By this treatment 11.5 g (87%) of the acetate is produced; b.p.=70° C./0,1 mm Hg.

GLC: One product only, 5% E.C.N.S.S.M. on Gas Chrom Q 100/120 mesh, 3 m inox ⅛, 140°.

I.R. (film, cm⁻¹) 1740 (C=O ester); 1660 (C=C); 950(s) and 945(w) (—CH=CH—, E conjugated).

EXAMPLE 9

Preparation of tetradecadiene-7E, 9E ol-1: (formula I, R=C₄H₉ and n=4) and its acetylated derivatives To the acetate obtained in Example 8 (5 g, 0.027 mole) in the presence of 10 ml of a solution of dilithium tetrachlorocuprate is added, at −10°, a N solution of the magnesium compound of (chloro-5' pentyloxy)-2 tetrahydropyran in T.H.F. (40.5 cm³) under the same conditions as those described in Example 3b) above.

After hydrolysis and evaporation of the solvent, the residue is treated with p-toluene sulfonic acid in methanol according to the same conditions as those in Example 4 which permit to obtain the tetradecadiene-7E, 9E ol-1. This latter, without being purified, is treated with acetic anhydride (3.6 g, 0.36 mole) in a conventional manner and produces 4 g (60%) of acetoxy-1 tetradecadiene-7E, 9E, b.p.=105°/0,1 mm Hg.

GLC: One product only, 3% FFAP on Gas Chrom G, 5 m inox ⅛, 200°.

I.R. (film, cm⁻¹) 1740 (C=O ester); —CH=CH—, E, conjugated: 985(s) and 955(w).

What is claimed is:

1. A process for the stereoselective preparation of sexual pheromones having an alcohol group and a conjugated diene structure of the trans-trans (E—E) stereochemical configuration corresponding to the following formula:

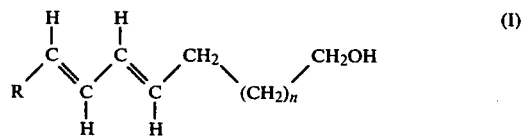

in which:

R represents a saturated linear alkyl radical having 1–4 carbon atoms and n is a number from 1 to 5, characterized by two stages, wherein in the first stage a magnesium derivative is prepared in a tetrahydrofuran medium said derivative corresponding to the following formula:

$$XMg-(CH_2)_n-CH_2 OP \quad (II)$$

in which:

X represents halogen which is Br or Cl, and P is a protective group and in a second stage at a temperature ranging from 0° to −20° C., an excess of said magnesium derivative is added to a tetrahydrofuran solution containing a copper catalyst and a trans-trans dienic compound corresponding to the following formula:

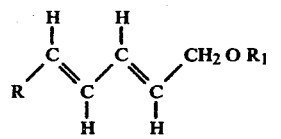

(III)

in which:

R has the same definition as above and $R_1$ is: —$COCH_3$, —$SO_2CH_3$ or —$SO_2C_6H_4CH_3$ and lastly, subjecting the product of the second stage to hydrolysis to liberate the protective group.

2. The process according to claim 1, wherein the magnesium derivative of formula (II) is obtained starting from a halogenated alkanol w—w', the OH function of which has been protected, wherein said halogenated alkanol is selected from the group consisting of chloro-3 propanol-1, bromo-3 propanol-1, chloro-4 butanol-1, bromo-4 butanol-1, chloro-5 pentanol-1, bromo-5 pentanol-1, chloro-6 hexanol-1, bromo-6 hexanol-1, chloro-7 heptanol-1 and bromo-7 heptanol-1.

3. The process according to claim 1, wherein the protective group P in formula (II) is tetrahydropyrannyl, tetrahydrofurannyl, trimethylsilyl, triethylsilyl triphenylmethyl, diphenylmethyl, benzyl or t-butyl.

4. The process according to claim 1, wherein the compound of formula (III) is obtained by acetylation, mesylation or tosylation of a dienic alcohol -2E, 4E, selected from the group consisting of hexadiene-2E, 4E ol-1; heptadiene-2E, 4E ol-1; octadiene-2E, 4E ol-1 and nonadiene-2E, 4E ol-1.

5. The process according to claim 1, wherein the copper catalyst is copper iodide, copper chloride, copper bromide or dilithium tetrachlorocuprate.

6. The process according to claim 1, wherein the quantity of the catalyst is from 0.01 to 0.06 mole, per mole of the compound of formula (III).

7. The process according to claim 1, wherein the excess of the magnesium derivative of formula (II) is at least 0.2 mole based on the molar quantity of the compound of formula (III).

8. The process according to claim 1, wherein the final concentration of the reactants in the tetrahydrofuran is from 0.1 N to 0.8 N, and preferably is about 0.5 N.

9. The process according to claim 1, wherein the hydrolysis for liberating the protective group is effectuated in an alcoholic medium in the presence of p-toluene sulfonic acid.

10. The process of claim 6, wherein the quantity of said catalyst is about 0.04 mole.

11. The process of claim 7, wherein said excess is from 0.25 to 0.6 mole.

* * * * *